United States Patent [19]

Mezei et al.

[11] Patent Number: 4,937,078
[45] Date of Patent: Jun. 26, 1990

[54] LIPOSOMAL LOCAL ANESTHETIC AND ANALGESIC PRODUCTS

[75] Inventors: Michael Mezei, Halifax, Canada; Adrienn Gesztes, Budapest, Hungary

[73] Assignee: Mezei Associates Limited, Nova Scotia, Canada

[21] Appl. No.: 236,724

[22] Filed: Aug. 26, 1988

[51] Int. Cl.$^5$ .............................................. A61K 37/22
[52] U.S. Cl. ................................... 424/450; 424/1.1; 514/817; 514/818
[58] Field of Search ................. 424/450, 1.1; 514/817, 514/818

[56] References Cited

U.S. PATENT DOCUMENTS

| | | | |
|---|---|---|---|
| 3,645,911 | 2/1972 | van Vesauw et al. | 264/4.6 |
| 3,804,776 | 4/1974 | Yazawa et al. | 427/213.3 |
| 4,016,100 | 4/1977 | Suzuki et al. | 264/4.3 |
| 4,048,310 | 9/1977 | Chen et al. | 514/873 X |
| 4,089,801 | 5/1978 | Schneider | 264/4.1 |
| 4,235,871 | 11/1980 | Papahadjopoulous et al. | 264/4.6 X |
| 4,342,826 | 8/1982 | Cole | 436/7 |
| 4,438,052 | 3/1984 | Weder et al. | 264/4.6 |
| 4,485,054 | 11/1984 | Mezei et al. | 264/4.6 |
| 4,532,089 | 7/1985 | MacDonald | 264/4.3 |
| 4,649,047 | 3/1987 | Kaswan | 424/78 |
| 4,721,612 | 1/1988 | Janoff et al. | 424/450 |
| 4,725,442 | 2/1988 | Haynes | 424/450 |
| 4,746,508 | 5/1988 | Carey et al. | 424/88 |

FOREIGN PATENT DOCUMENTS

| | | |
|---|---|---|
| 00084898 | 8/1983 | European Pat. Off. |
| 85/306641.8 | 4/1987 | European Pat. Off. |
| 3335701A1 | 4/1981 | Fed. Rep. of Germany |
| WO85/03640 | 8/1985 | PCT Int'l Appl. |
| 2050833A | 1/1981 | United Kingdom |

OTHER PUBLICATIONS

Bangham et al., "Diffusion of Univalent Ions Across the Lamellae of Swollen Phospholipids", J. Mol. Biol. 13:238–252 (1965).
Bangham et al., "Osmotic Properties and Water Permeability of Phospholipid Lipid Crystals, Chem. Phys. Lipids, 1:225–246 (1967).
Batzri et al., "Single Bilayer Liposomes Prepared Without Sonication", Biochim. et Biophys. Acta, 298:1015–1019.
Bangham et al., "Preparation and Use of Liposomes as Models of Biological Membranes", Methods in Membrane Biology, 6 (London 1974).
Papahadjopoulos et al, "Effects of Local Anesthetics on Membrane Properties", Biochim et Biophys. Acta, 394:504–519 (1975).
Theoharides, "Liposomes as Carriers of Biologically Active Molecules", Folia Bioch. et Biol. Graeca, Special Issue, vol. XIV, pp. 11–21 (1978).
Mezei et al., "Liposomes–A Selective Drug Delivery System for the Topical Route of Administration", Life Sciences, vol. 26, pp. 1473–1477 (1980).
Okano et al., "Duration of the Local Anesthetic Action of Dibucaine by Liposomes and Its Mechanism", Yakugaku Zasshi, vol. 100 (11), pp. 1097–1103 (1980).
Chemical Abstracts, vol. 97, No. 22 (1982), Abstract No. 188156k.
"The Effect of Local Anaesthetics on the Osmotic Fragility of Liposomes", Biochemical Pharmacology, vol. 31, No. 18, pp. 2999–3000 (1982).
Mezei et al., "Liposomes—A Selective Drug Delivery System for the Topical Route of Administration: Gel Dosage Form", J. Pharm. Pharmacol., 1982, 34:473–474.
Cecil–"Textbook of Medicine", vol. 1 (1982), pp. 1276–1278.
Seelig, Biochimica et Biophysica Acta 899 (1987) 196–204.
Kuroda et al., Biochimica et Biophysica Acta 903 (1987) 395–410.
Bianconi et al., Biochemical and Biophysical Research Communications, vol. 152(1):344–350 (1988).
Seelig et al., Biochimica et Biophysica Acta 939 (1988) 267–276.
Gesztes et al., Topical Anesthesia of the Skin by Liposome-Encapsulated Tetracaine, Anesth Analg, vol. 67:1079–1081 (1988).
Mezei, "Liposomes in the Topical Application of Drugs: a Review", Liposomes as Drug Carriers, edited by G. Gregoriadis, John Wiley & Sons Ltd., NY (1988) pp. 663–677.
Ohki, Biochimica et Biophysica Acta, 777 (1984) 56–66.
Schlieper et al., Biochemical Pharmacology, vol. 32, No. 5, pp. 799–804 (1983).
Simmonds et al., Biochimica et Biophysica Acta, 813 (1985) 331–337.
Krause-Friedmann et al., Biochimica et Biophysica Acta, 799 (1984) 195–198.
Dalili et al. Clin. Pharm. Ther., 12:9–919 (1971).
Adriani et al., Anesth. Analg., 50:834–841 (1971).
Juhlin et al., Acta Dermatovener 59:556–559 (1979).
Wildsmith et al., Clinics in Anaesthesiology, 4:527–537 (1986).
Ehrenstrom Reiz et al., Acta Anaesth. Scand. 26:596–598 (1982).
Evers et al., Br. J. Anaesth. 58:997–1005 (1985).
Juhlin et al., Acta Dermatovener 60:544–546 (1980).

Primary Examiner—Ellis P. Robinson
Assistant Examiner—P. L. Prater
Attorney, Agent, or Firm—Banner, Birch, McKie & Beckett

[57] ABSTRACT

Liposome encapsulated local anesthetic or analgesic agents when applied to skin or mucous membranes provided greater local anesthesia and analgesia than the same agents incorporated in conventional vehicles i.e., ointment, cream or lotion.

14 Claims, No Drawings

LIPOSOMAL LOCAL ANESTHETIC AND ANALGESIC PRODUCTS

BACKGROUND OF THE INVENTION

1. Field of the Invention

The present invention relates to a method for providing local anesthesia using liposomal encapsulated anesthetic and analgesic drugs.

2. Description of Related Art

Liposomes are lipid vesicles composed of membrane-like lipid layers surrounding aqueous compartments. Liposomes are widely used to encapsulate biologically active materials for a variety of purposes, e.g. they are used as drug carriers. Depending on the number of lipid layers, size, surface charge, lipid composition and methods of preparation various types of liposomes have been utilized.

Multilamellar lipid vesicles (MLV) were first described by Bangham, et al., (J. Mol. Biol. 13:238–252, 1965). A wide variety of phospholipids form MLV on hydration. MLV are composed of a number of bimolecular lamellar interspersed with an aqueous medium. The lipids or lipophilic substances are dissolved in an organic solvent. The solvent is removed under vacuum by rotary evaporation. The lipid residue forms a film on the wall of the container. An aqueous solution generally containing electrolytes and/or hydrophilic biologically active materials are added to the film. Agitation produces larger multilamellar vesicles. Small multilamellar vesicles can be prepared by sonication or sequential filtration through filters with decreasing pore size. Small unilamellar vesicles can be prepared by more extensive sonication. An improved method of encapsulating biologically active materials in multilamellar lipid vesicles is described in U.S. Pat. No. 4,485,054.

Unilamellar vesicles consist of a single spherical lipid bilayer entrapping aqueous solution. According to their size they are referred to as small unilamellar vesicles (SUV) with a diameter of 200 to 500 A; and large unilamellar vesicles (LUV) with a diameter of 1000 to 10,000 A. The small lipid vesicles are restricted in terms of the aqueous space for encapsulation, and thus they have a very low encapsulation efficiency for water soluble biologically active components. The large unilamellar vesicles, on the other hand, encapsulate a high percentage of the initial aqueous phase and thus they can have a high encapsulation efficiency. Several techniques to make unilamellar vesicles have been reported. The sonication of an aqueous dispersion of phospholipid results in microvesicles (SUV) consisting of bilayer or phospholipid surrounding an aqueous space (Papahadjopoulos and Miller, Biochem. Biophys. Acta., 135: 624–238, 1968). In another technique (U.S. Pat. No. 4,089,801) a mixture of a lipid, an aqueous solution of the material to be encapsulated, and a liquid which is insoluble in water, is subjected to ultrasonication, whereby liposome precursors (aqueous globules enclosed in a monomolecular lipid layer), are formed. The lipid vesicles then are prepared by combining the first dispersion of liposome precursors with a second aqueous medium containing amphiphilic compounds, and then subjecting the mixture to centrifugation, whereby the globules are forced through the monomolecular lipid layer, forming the biomolecular lipid layer characteristic of liposomes.

Alternate methods for the preparation of small unilamellar vesicles that avoid the need of sonication are the ethanol injection technique (S. Batzri and E. E. Korn, Biochem. Biophys. Acta. 298: 1015–1019, 1973) and the ether injection technique (D. Deamer and A. D. Bangham, Biochem. Ciophys. Acta. 443: 629–634, 1976). In these processes, the organic solution of lipids is rapidly injected into a buffer solution where it spontaneously forms liposomes—of the unilamellar type. The injection method is simple, rapid and gentle. However, it results in a relatively dilute preparation of liposomes and it provides low encapsulation efficiency. Another technique for making unilamellar vesicles is the so-called detergent removal method (H. G. Weder and O. Zumbuehl, in "Liposome Technology": ed. G. Gregoriadis, CRC Press Inc., Boca Raton, Florida, Vol. I, Ch. 7, pg. 79–107, 1984). In this process the lipids and additives are solubilized with detergents by agitation or sonication yielding defined micelles. The detergents then are removed by dialysis.

Multilamellar vesicles can be reduced both in size and in number of lamellae by extrusion through a small orifice under pressure, e.g., in a French press. The French press (Y. Barenholz; S. Amselem an D. Lichtenberg, FEBS Lett. 99: 210–214, 1979), extrusion is done at pressures of 20,000 lbs/in at low temperature. This is a simple, reproducible, nondestructive technique with relatively high encapsulation efficiency, however it requires multilamellar liposomes as a starting point, that could be altered to oligo- or unilamellar vesicles. Large unilamellar lipid vesicles (LUV) can be prepared by the reverse phase evaporation technique (U.S. Pat. No. 4,235,871, Papahadjopoulos). This technique consists of forming a water-in-oil emulsion of (a) the lipids in an organic solvent and (b) the substances to be encapsulated in an aqueous buffer solution. Removal of the organic solvent under reduced pressures produces a mixture which can then be converted to the lipid vesicles by agitation or by dispersion in an aqueous media.

U.S. Pat. No. 4,016,100, Suzuki et al., describes still another method of entrapping certain biologically active materials in unilamellar lipid vesicles by freezing an aqueous phospholipid dispersion of the biologically active materials and lipids. All the above liposomes, made prior to 1983, can be classified either as multilamellar or unilamellar lipid vesicles. A newer type of liposomes is referred to as multivesicular liposomes (S. Kim, M. S. Turker, E. Y. Chi, S. Sela and G. M. Martin, Biochim. Biophys. Acta. 728: 339–348, 1983). The multivesicular liposomes are spherical in shape and contain internal granular structures. A lipid bilayer forms the outermost membrane and the internal space is divided up into small compartments by bilayer septrum. This type of liposomes required the following composition: an amphiphatic lipid with net neutral charge, one with negative charge, cholesterol and a triacylglycerol. The aqueous phase containing the material to be encapsulated is added to the lipid phase which is dissolved in chloroform and diethyl ether, and a lipid-in-water emulsion is prepared as the first step in preparing multivesicular liposomes. Then a sucrose solution is shaken with the water-in-lipid emulsion; when the organic solvents are evaporated liposomes with multiple compartments are formed.

For a comprehensive review of types of liposome and methods for preparing them refer to a recent publication "Liposome Technology" Ed. by G. Gregoriadis., CRC Press Inc., Boca Raton, Florida, Vol. I, II, and III 1984.

Liposomes, vesicles of phospholipid membranes, have been studied in recent years as a way of altering the pharmacokinetic properties of encapsulated drugs. A few studies have focused on their potential as drug carriers in topical preparations, for example involving corticosteriods, econazole, progesterone and methotrexate. Liposomal formulations of these materials were found which when applied topically delivered more of these drugs into the skin than conventional vehicles, (enhanced penetration) while at the same time localizing their effect at the desired site of action (enhanced localization) (M. Mezei in "Liposomes as Drug Carriers" ed. G. Gregoriadis, John Wiley & Sons Ltd., New York 1988, pages 663–677).

Topical anesthetics are agents that reversibly block nerve conduction causing numbness and cessation of pain even after major stimuli. A topical analgesic agent is a substance which relieves pain without necessarily causing numbness, or which can relieve topical pain of a minor nature, but not of a great degree (Fed. Register 44, 69768–69866, 1979). These drugs are therefore used to treat or prevent pain. For operations of a peripheral or minor nature involving the skin, like removal of superficial skin lesions and plastic surgery, or intradermal allergen testing, split skin grafting, treatment of painful ulcers, venipuncture—the ideal way of anesthesia would be the topical application of local anesthetics.

The commercially available topical anesthetic preparations however, are not completely suitable for this purpose. Studies of Dalili and Adriani (Clin. Pharm. Ther., 12: 913–919, 1971) provided the first experimental evidence that manufactured preparations containing local anesthetics intended for use on the surface of the skin often lack a desired degree of efficacy. The preparations were tested on normal skin and on ultraviolet light burned skin for the ability to block itching and pricking induced by electrical stimulation. The only preparation judged sufficiently effective was one containing 20% benzocaine. But even the effect of this preparation disappeared within 60 seconds after it has been wiped off the test site. The authors indicated several possible reasons for the lack of efficacy, including the low concentration of the active ingredient, possible chemical change or interaction, for example, with other components and the penetration-preventing effect of the vehicle formulation used (J. Adriani and H. Dalili., Anesth., Analg. 50: 834–841, 1971).

At present, the most successful commercially available preparation for dermal anesthesia is a lidocaine-prilocaine cream, first reported by Juhlin et al. (Acta Derm Venereol. 59: 556–559, 1979). The cream consists of an emulsion containing 5% by weight of the eutectic mixture of lidocaine and prilocaine bases (EMLA) in water, thickened with Carbopol® (G. M. E. Ehrenstrom Reiz and SLA Reiz., Acta Anaesth. Scand., 26: 596–598, 1982). An application time of 60 minutes under occlusion achieves complete anesthesia to pinpricks, and the anesthetic effect lasts one to two hours (H. Evers et al., Br. J. Anaesth., 58: 997–1005, 1985).

In general, to achieve adequate local anesthesia of the skin using known preparations, a relatively excessive amount of drug, a prolonged application period or invasive methods are required. For adequate surgical anesthesia, the local anesthetic must be injected subcutaneously in order to reach sensory nerve endings lying in the dermis. When injecting a local anesthetic, pain is produced by the needle's penetration and by the deposition of the anesthetic solution. Distortion of the wound or performing the infiltration of large areas can also be problems in surgical cases (L. Juhlin, H. Evers, and F. Broberg., Acta Derm. Venereol., 60: 544–546, 1980).

In contrast to anesthetizing the skin, anesthesia of mucous membrane covered surfaces can be produced by topical application of local anesthetics quickly and easily. Unfortunately, rapid absorption of the local anesthetic through these surfaces into the circulatory system may reduce the duration of local anesthetic action, and since these drugs have low therapeutic ratios, may possibly cause systemic toxicity (J. A. Wildsmith, A. P. Rubin and D. B. Scott., Clin. Anaesth., 4: 527–537, 1986).

Thus, there is a continuing need in the art of local anesthesia for a preparation that is safe, yet effective on either unbroken skin, or on mucous membranes which provides a proper rate of drug permeation without discomfort or a risk of systemic reactions.

Local anesthetic agents previously have been encapsulated into liposomes. (Papahadjopoulos et al., Biochim. Biophys Acta, 394: 504–519, 1975). However, the liposome encapsulated local anesthetic was not used for producing local anesthesia or analgesia but rather was prepared as a way of studying the drug's mechanism of action, i.e. the interaction of the local anesthetic with the phospholipid bilayers, which in effect served as a model for a cellular membrane.

DESCRIPTION OF THE INVENTION

The present invention broadly relates to the use of liposomes for improving the effect on a mammal of topically applied preparations of local anesthetics and analgesics by enhancing the penetration (i.e. increasing cutaneous absorption) and localization (i.e. decreasing systemic absorption) of the anesthetic and analgesic agents.

The present invention may be used to provide local anesthetic and analgesic treatment for both human and veterinary purposes. Local anesthetics, as amphipathic agents, are good candidates for entrapment in the phospholipid bilayers of a liposome. Any anesthetic and analgesic agent or drug suitable for topical or local application can be used in the present invention including benzocaine, xylocaine, ketocaine, methyl salicylate, trolamine salicylate, lidocaine, prilocaine, tetracaine, pramoxine (tronothane) and dibucane. Tetracaine is a particularly useful agent because it is a potent topical anesthetic and owing to its relatively large hydrophobic moiety, it is easily encapsulated by phospholipid bilayers.

The amount of the anesthetic or analgesic agent or drug to be included in the liposomal preparation is not, per se, critical and can vary within wide limits depending inter alia on the particular agent, the intended application and the lipid used. Generally, the anesthetic or analgesic agent may be included in an amount of between about 0.1 to 10% by wt. of the liposomal preparation and more usually may be included in an amount of between 0.3 and 5.0% by wt.

Materials and procedures for forming liposomes are well-known to those skilled in the art and need not be described herein in detail. Reference is made to U.S. Pat. Nos. 4,485,054 and 4,761,288, which are hereby incorporated by reference, for a disclosure of preferred preparation techniques. Generally, the desired anesthetic or analgesic agent to be encapsulated is dissolved or dispersed in a lipid-containing organic solvent. Phospholipids are particularly useful, such as those selected from the group consisting of phosphatidylchloines, lysophosphatidylchloines, phosphatidylserines, phosphatidylethanolamines, and phosphatidylinositols. Such phospholipids often are modified using for example, a modifying agent selected from the group consisting of cholesterols, stearylamines and tocopherols. The solvent then is evaporated, typically under a reduced pressure, to yield a thin lipid film containing the anesthetic or analgesic. Afterwards, the film is hydrated, with agitation, using a aqueous phase containing any desired electrolytes and lipid vesicles entrapping the anesthetic or analgesic are produced. As recognized by those skilled in the art, while certain materials and procedures may give better results with certain drugs, the use of particular materials and procedures are not narrowly critical and optimum conditions can be determined using routine testing. Although some of the liposome formulations acquire a gel-like consistency upon cooling to room temperature in the absence of any adjuvants, the present invention contemplates the use of conventional thickeners and gelling agents to provide a preparation having any desired consistency for topical application. Additionally, a preservative or antioxidant often will be added to the preparation.

A particular feature of the present invention is that a more pronounced cutaneous anesthetic or analgesic effect is obtained in the patient with a smaller amount of the active anesthetic or analgesic agent than compared with prior topical preparations. While not wishing to be bound to any theory, it is thought that the lipid vesicles facilitate transport of the anesthetic or analgesic drug through the stratum corneum barrier. Thus, preparations containing from 0.1 to 3.0% by wt. of the anesthetic or analgesic agent may be useful. The low drug concentration should permit its use as a safe and effective over-the-counter medication for painful skin disorders. In most cases, the anesthetic or analgesic agent comprises from about 5 to about 25% by wt. of the lipid, i.e. the phospholipid, neutral lipid, surfactant or similar material having the amphiphilic character needed to form the lipid vesicles.

The amount of the liposomal preparation to be applied to the patient can vary within wide limits depending inter alia an the particular site of application and the desired duration of effect. Generally, application of between about 0.005 to 0.5 g of liposomal preparation per square centimeter of surface to be anesthesized should be sufficient, with an amount of between 0.01 to 0.05 g/cm$^2$ being useful in many cases. Preferably, the liposomal preparations of the present invention are applied topically under occlusion to obtain enhanced effect.

The following examples are illustrative of the present invention and are not to be regarded as limiting. In the examples, several anesthetic agents, e.g. benzocaine, lidocaine, prilocaine, lidocaine-prilocaine eutectic mixtures, tetracaine and dibucaine, were encapsulated into liposomes using the procedure described in Mezei et al. U.S. Pat. No. 4,485,054. In order to increase the effective concentration of the encapsulated drug, e.g. with benzocaine, lidocaine and dibucane, where a reduced solubility restricted, to some extent, the upper concentration, the multiphase liposomal drug delivery system described and claimed in Mezei, U.S. Pat. No. 4,761,288 was utilized. Most of the time the base (and not the salt) of the anesthetic agent was used for preparing the liposomal product. It should be understood that all of the parts, percentages, and proportions referred to herein and in the appended claims are by weight unless otherwise indicated. The following examples demonstrate the formulas and the activity of selected anesthetic agents in liposome form versus ointment or cream form.

EXAMPLE 1

| Formula: | |
| --- | --- |
| TetracaCine (base) | 0.5 g |
| Soy phosphatidylcholine | 7.0 g |
| Cholesterol | 0.5 g |
| Stearic acid | 0.7 g |
| Ethanol (95%) | 10.0 ml |
| Propylene glycol | 7.0 ml |
| Solution of sodium chloride (0.45 wt. %) and sodium bicarbonate (0.65 wt. %) | 83.0 ml |

The tetracaine base (pharmacopoeal grade), phosphatidylcholine (NC-95-H, American Lecithin Co., Atlanta, Georgia), cholesterol (Sigma Chem. Co.) and stearic acid (Fisher Scientific Co.) were dissolved in a chloroform:methanol (2:1 v/v) solvent solution in a pear-shaped flask, and small glass beads (100 g) were added. The solvent was evaporated to dryness in a rotary evaporator at 30° C. and under a reduced pressure, until a smooth, thin lipid film was obtained on the surface of the flask and the glass beads. The film then was hydrated with an aqueous phase prepared by mixing the aqueous solution of 0.65 wt. % NaHCO$_3$, and 0.45 wt. % NaCl, the ethanol and the propylene glycol, by shaking for 30 minutes in a Lab-Line Orbit Environ-Shaker at 55° C. The liposomes were separated from the glass beads by filtering the hydrated preparation through a Buchner funnel without using filter paper.

EXAMPLE 2

| Formula: | |
| --- | --- |
| Lidocaine | 2.0 g |
| Soy phosphatidylcholine | 9.0 g |
| Tocopherol acetate | 0.24 g |
| Hydroxypropylmethylcellulose | 1.5 g |
| Aqueous solution of sodium chloride (0.45 wt. %) and sodium bicarbonate (0.65 wt. %) | 100.0 ml |

The lidocaine, soy phosphatidylcholine and tocopherol acetate were dissolved in a chloroform:methanol (2:1 v/v) solvent solution in a pear-shaped flask containing 100 g of small glass beads. The solvent was evaporated in a rotary evaporator at 30° C. and under reduced pressure until a thin, smooth film of the lipid and lidocaine was obtained on the surface of the glass beads and the wall of the flask. The resulting lipid film was hydrated at 55° C. using the aqueous sodium chloride and sodium bicarbonate solution in an environment shaker for 30 minutes. The hydroxypropylmethylcellulose was added to the preparation within 5 seconds after the lipid film and aqueous solution were mixed.

EXAMPLE 3

| Dibucaine | 1.0 g |
| --- | --- |
| Soy phosphatidylcholine | 8.0 g |
| Tocopherol acetate | 1.0 g |
| Hydroxypropylmethylcellulose | 1.0 g |
| Tween ®-80 | 1.0 g |

| -continued | |
|---|---|
| CaCl₂ solution 0.8 mM | 100.0 ml |

The method of preparation was substantially the same as that described above for Example 2; Tween ®-80 was added last to the liposomal product.

EXAMPLE 4

In a manner similar to the preceding examples, several other compositions were prepared using:
 (a) different local anesthetic agents (e.g. benzocaine, prilocaine and a lidocaine-prilocaine eutectic mixture) with various concentrations of the active ingredient (i.e., 0.5 to 5 wt. %);
 (b) phosphatidycholines of different origin and at various concentrations (i.e., 2–15 wt. %);
 (c) cholesterol or tocopherol lipid vesicle modifiers in different concentrations (i.e., 0.5–5 wt. %);
 (d) buffer solutions with various pH's and electrolyte contents;
 (e) various viscosity inducing agents (e.g. methylcellulose, Carbopol ®, etc.) and
 (f) various preservatives or antioxidant agents (e.g. benzoic acid, methyl and propyl paraben butylated hydroxyanisole (BHA), benzylalcohol, etc.);

The efficacy of the various local anesthetic agent preparations were tested in liposomal form against a commercial cream preparation or an ointment prepared using the same drug.

Evaluation of local anesthetic/analgesic activity

A protocol for human experiments was approved by the Ethics Committee for Human Research of the Faculty of Health Professions of Dalhousie University, Halifax, Canada. Healthy adult volunteers with no skin disorders or previous history of allergic sensitivity to local anesthetics were asked to participate in the study. Twelve subjects in each experimental group having ages ranging from 25 to 60 years were investigated.

Example A: Tetracaine (0.5 wt. %) Liposomal Preparation

Liposomal preparation containing about 0.5 wt. % tetracaine base (formula as Example No. 1) and Pontocaine ® cream (tetracaine hydrochloride cream U.S.P., equivalent to 1% tetracaine base, manufactured by Winthrop Laboratories Aurora, Ontario, Lot No. 120 BL) were compared. A 0.2 ml volume of the liposomal preparation was applied to a 10 cm² area marked by ink on the volar surface of one forearm of each of the volunteers and covered with Blenderm ® tape (3M Co., St. Paul, Minnesota) to form an occlusive dressing. The same amount of Pontocaine ® cream was applied to the other arm of each volunteer in the same manner. The samples of the liposomal preparation and the commercial preparation were randomly numbered, and the number of applied preparations recorded for each subject. The identity of the preparations was not known for the subjects or for the evaluator so as to maintain the "double blind" study design.

The samples were applied for 30 minutes in the first group of volunteers and for 60 minutes in the second group. After each of these time intervals the covering tape was removed and the tested area wiped dry with a tissue paper. Onset and duration of anesthesia at the test sites were tested using the pin-prick technique, described in detail by Lubens et al. (Am. J. Dis. Child., 128: 192–194, 1974). At each test period, each skin test area was pricked ten times using a relatively blunt sterile needle, to allow each subject to discriminate between the perception of touch and pain. Ten painless pricks at the time of the test was indicative of complete anesthesia. Sensitivity for each subject was confirmed by pin-pricking near to the test site areas before applying the samples to be tested. Testing score indexes were obtained from each of the volunteers by noting the number of painfree pin-pricks out of the 10 in both test areas. Testing was done immediately after the preparations had been removed from the test site, and then at 30 min., 1 h, 2 h, and 4 h afterwards. Results are reported in Tables 1 and 2.

As shown by the results in Tables 1 and 2 the liposome preparation containing 0.5% tetracaine base was effective in producing dermal anesthesia. After the onset of anesthesia the perception of pain was greatly reduced, although the pressure could be felt. The perception of cold also was observed to disappear at the "numb" test sites (by testing with a cold metal rod). Sensitivity of nerve fibers conveying the sensations of pain, cold, warmth, touch and deep pressure to local anesthetic action is differential. This is correlated with the fiber diameter, that increases from the fibers conveying the sensation of pain to those conveying deep pressure. Pain fibers are the first to be blocked, followed by sensations of cold, warmth, touch and deep pressure. Apparently, the absorbed doses in these tests were high enough only to block the pain and cold fibers, having no or little effect on touch or pressure sensations.

The results also show that the duration of application influences the intensity and duration of the anesthetic effect. On removal of the preparation after 30 minutes of application, the anesthesia was less pronounced, than after a one hour period of application. In both cases, the anesthesia effect improved with time after initial application. Since the onset of anesthetic action is not necessarily immediate, the preparation can be dispensed for administration suitably in advance of any painful procedure. A maximum in anesthetic effect was reached in both the 30 minutes and 1 hour application time groups about two hours after removal of the preparation at an average painless score of 8.25 and 9.5 respectively. Approximately, this level of anesthesia was maintained until the end of the experiments. Tests were conducted only up to 4 hours after removal of the preparations, but the anesthesia provided by the present invention was reported by the volunteers to persist longer, from 5 to 8 hours, depending on the application time.

Considerable inter-individual variations were observed in the onset time of action. Painless scores in the 30 minutes and 1 hour period of application time groups at the time of removal were, respectively, at or above 7 in 25% and 50% of all the subjects tested (N=12). Pontocaine cream, the control preparation, was found to be relatively ineffective over the entire test period, in agreement with findings of Dalili and Adriani (Cin. Pharm. Ther., 12: 913–919, 1971).

Statistical analysis of the data by paired t-tests indicated a statistically highly significant difference in favor of the liposomal tetracaine over the commercial preparation (See Tables 1 and 2).

Example B: Lidocane (2 wt. %) Liposomal Preparation

Liposomes with about 2 wt. % lidocaine (preparation as Example No. 2) were compared to a placebo, which consisted of "empty" liposomes with the same composition as that of the active preparation but without lidocaine. A comparison of the 2 wt. % lidocaine liposomes also was carried out with a control, which contained 2 wt. % lidocaine incorporated in Dermabase ® as the vehicle. In both groups, the length of application of liposomal and control preparations was one hour. The procedures of Example A were repeated and the results are reported in Tables 3 and 4.

The anesthetic effect of the 2 wt. % lidocaine liposomes compared to the placebo, as measured by the painless scores, is shown in Table 3. Similarly to the tetracaine liposomal preparation, lidocaine encapsulated in liposomes produced anesthesia in the intact skin after topical application.

TABLE 1

Mean painless scores at different times of observation after an initial 30 minutes application period under occlusion of 0.5% tetracaine liposome preparation and Pontocaine ® cream.
Number of volunteers = 12
Statistical analysis by paired t-tests

| Time | Lipsome preparaton Mean | SD | Pontocaine ® cream Mean | SD | P |
|---|---|---|---|---|---|
| at removal | 2.75 | 3.25 | 0.25 | 1.73 | 0.0644 |
| 30 Min | 5.50 | 3.94 | 1.08 | 1.98 | 0.0117 |
| 1 hour | 6.75 | 3.28 | 1.08 | 1.68 | <0.0001 |
| 2 hours | 8.25 | 2.45 | 1.08 | 1.31 | <0.0001 |
| 4 hours | 8.33 | 2.31 | 0.25 | 0.62 | <0.0001 |

TABLE 2

Mean painless scores at different times of observation after an initial 1 hour application period under occlusion of 0.5% tetracaine liposome preparation and Pontocaine ® cream
Number of volunteers = 12
Statistical analysis by paired t-tests

| Time | Lipsome preparation Mean | SD | Pontocaine ® cream Mean | SD | P |
|---|---|---|---|---|---|
| at removal | 6.25 | 3.65 | 0.08 | 0.29 | <0.0001 |
| 30 min | 8.08 | 2.27 | 0.41 | 0.99 | <0.0001 |
| 1 hour | 8.83 | 1.47 | 0.25 | 0.62 | <0.0001 |
| 2 hours | 9.50 | 0.67 | 0.33 | 1.15 | <0.0001 |
| 4 hours | 8.75 | 1.48 | 0.16 | 0.57 | <0.0001 |

The pain and cold sensations were greatly reduced, but not the perception of pressure. The intensity of the anesthetic effect again continued to increase after the removal of the preparation, and reached its maximum value one hour later. The differences between the placebo and the liposome-encapsulated lidocaine preparation were statistically significant at every time point (Table 3). Similar results to the placebo experiment and to Example A were obtained when liposomal lidocaine was compared to lidocaine in a Dermabase ® vehicle (see Table 4).

Example C: Other Preparations

Table 5 presents and compares the liposomal tetracaine preparation of the present invention with several other anesthetic preparations designed for topical application.

Thus, while certain specific embodiments of the invention have been described with particularity herein, it will be recognized that various modifications thereof will occur to those skilled in the art and it is to be understood that such modifications and variations are to be included within the purview of this application and the spirit and scope of the appended claims.

TABLE 3

Mean painless scores at different times of observation after an initial 1 hour application period under occlusion of 2% lidocaine liposome preparation and placebo
Number of volunteers = 12
Statistical analysis by paired t-tests

| Time | Lipsome preparation Mean | SD | Placebo Mean | SD | P |
|---|---|---|---|---|---|
| at removal | 4.08 | 4.42 | 1.08 | 1.51 | 0.0337 |
| 30 min | 6.08 | 4.14 | 1.33 | 1.92 | 0.0040 |
| 1 hour | 7.25 | 3.86 | 2.08 | 2.23 | 0.0040 |
| 2 hours | 6.16 | 3.35 | 1.58 | 2.81 | 0.0062 |
| 3 hours | 5.33 | 3.17 | 1.16 | 2.04 | 0.0042 |

TABLE 4

Mean painless scores at different times of observation after an initial 1 hour application period under occlusion of 2% lidocaine liposome preparation and 2% lidocaine in Dermabase ® (control)
Number of volunteers = 5
Statistical analysis by paired t-tests

| Time | Lipsome preparation Mean | SD | Dermabase ® (control) Mean | SD | P |
|---|---|---|---|---|---|
| at removal | 6.2 | 3.56 | 1.8 | 2.49 | 0.103 |
| 30 min | 7.4 | 3.71 | 2.6 | 1.67 | 0.018 |
| 1 hour | 9.8 | 0.45 | 3.6 | 0.89 | <0.001 |
| 2 hours | 8.6 | 1.14 | 3.2 | 1.30 | <0.001 |
| 3 hours | 4.6 | 3.13 | 2.2 | 2.17 | 0.051 |

TABLE 5

Comparison of liposomal tetracaine preparation with other formulations for topical anesthesia

| Reference | Drug | Vehicle | Onset time | Duration | Dosage | Side Effect |
|---|---|---|---|---|---|---|
| Monash, S. Arch. Dermatol. 76:752-56, 1957. | 5% tetracaine | ointment | 1.5 h | 3.5 h | additional ointment hourly | |
| Lubens, H. M. Sanker, J. F. Ann, Allerg. 22:37-41, 1964. | 30% xylocaine | "acid mantle cream" | 2 h— 4 h— (application) | 0.5 h 3 h | "liberal amount" | |
| Brechner, V. L. et al. Ann. N.Y. Acad. Sci. 141:524-31, 1967. | 5-33% tetracaine | dimethyl sulfoxide (DMSO) | 0.5 h | 3 h | 1 ml to 5 × 5 cm area | pruritis hypersensitivity |
| Ohlsen, L. Englesson, S. Brit. J. Anaesth. 52:413-16, 1980. | 10% ketocaine | isopropanol glycerol water | 1-10 h | several hours | 5.3 ml to 8 × 10 cm area | erythema oedema |
| Evers. H. et al. Brit J. Anaesth. 58:997-1005, 1985. | 5% lidocaine-prilocaine (EMLA) | oil in water emulsion | 1 h | 1 h | 1 g to 6.25 cm$^2$ area | |
| This Invention | 0.5% tetracaine | liposome | 0.5-1 h | at least 4 h | 0.2 ml to 3 × 3 | |

TABLE 5-continued

| Comparison of liposomal tetracaine preparation with other formulations for topical anesthesia | | | | | | |
|---|---|---|---|---|---|---|
| Reference | Drug | Vehicle | Onset time | Duration | Dosage | Side Effect |
| | | preparation | | | cm area | |

We claim:

1. A method for providing local anesthesia or analgesia to a mammal which comprises topically applying a composition to said mammal in an amount of between about 0.005 to 0.5 g/cm$^2$ of surface to be anesthesized, said composition containing an anesthetic or analgesic agent selected from the group consisting of benzocaine, xylocaine, ketocaine, methyl salicylate, trolamine salicylate, lidocaine, prilocaine, tetracaine, pramoxine and dibucaine, encapsulated within lipid vesicles in an amount of between about 0.1 to 10% by wt. of said composition.

2. The method of claim 1 in which the composition contains multilamellar lipid vesicles.

3. The method of claim 1 wherein the lipid vesicles comprise unilamellar lipid vesicles.

4. The method of claim 1 wherein the lipid vesicles are multivesicular.

5. The method of claim 1 wherein said lipid vesicles are prepared using a phospholipid.

6. The method of claim 5 wherein the phospholipid is selected from the group consisting of phosphatidylchloines, lysophosphatidylchloines, phosphatidylserines, phosphatidylethanolamines, and phosphatidylinositols.

7. The method of claim 6 wherein the phospholipid is provided in admixture with a modifying agent selected from the group consisting of cholesterols, stearylamines and tocopherols.

8. The method of claim 7 wherein the anesthestic or analgesic agent is selected from the group consisting of benzocaine, xylocaine, ketocaine, lidocaine, prilocaine, tetracaine and dibucaine.

9. The method of claim 8 wherein the composition contains said anesthestic or analgesic agent in an amount between about 0.3% and 5.0% by weight.

10. A pharmaceutical composition comprising lipid vesicles having a topical anesthetic or analgesic agent selected from the group consisting of benzocane, xylocaine, ketocaine, methyl salicylate, trolamine salicylate, lidocaine, prilocaine, tetracaine and pramoxine, encapsulated therein in an amount of between about 0.1 to 10% by wt. of said composition.

11. The composition of claim 10 wherein the lipid vesicles are multilamellar.

12. The composition of claim 10 wherein the lipid vesicles are unilamellar.

13. The composition of claim 10 wherein the lipid vesicles are multivesicular.

14. A method for providing local anesthesia or analgesia to a mammal which comprises topically applying to said mammal a composition containing phospholipid vesicles encapsulating 0.1 to 10% by wt. of an anesthetic or analgesic agent, wherein said composition is applied in an amount between about 0.005 to 0.5 g/cm$^2$ of surface to be anesthesized.

* * * * *